(12) United States Patent
Khalifah et al.

(10) Patent No.: US 6,342,500 B1
(45) Date of Patent: Jan. 29, 2002

(54) POST-AMADORI INHIBITORS OF ADVANCED GLYCATION REACTIONS

(75) Inventors: Raja Khalifah, Overland Park; Aaron Ashley Booth, Prairie Village, both of KS (US)

(73) Assignee: Kansas University Medical Center, Kansas City, KS (US)

( * ) Notice: Subject to any disclaimer, the term of this patent is extended or adjusted under 35 U.S.C. 154(b) by 0 days.

(21) Appl. No.: 09/518,308

(22) Filed: Mar. 3, 2000

Related U.S. Application Data (60) Provisional application No. 60/123,011, filed on Mar. 5, 1999.

(51) Int. Cl.$^7$ .................. C07D 213/02; C07D 239/24; A61K 31/44; A61K 31/506; A61P 3/10
(52) U.S. Cl. .................. 514/256; 514/333; 546/255; 546/256; 544/333
(58) Field of Search .................. 544/337, 333; 548/314.7; 546/255, 256; 514/2, 82, 333, 256

(56) References Cited

U.S. PATENT DOCUMENTS

| | | | |
|---|---|---|---|
| 4,665,192 A | 5/1987 | Cerami | 548/336 |
| 5,211,643 A | 5/1993 | Reinhardt et al. | 604/403 |
| 5,399,560 A | 3/1995 | Cerami et al. | 514/242 |
| 5,474,992 A | 12/1995 | Ogata et al. | 514/100 |
| 5,869,444 A | 2/1999 | Klein | 514/2 |
| 5,985,857 A | 11/1999 | Hudson et al. | 514/89 |

FOREIGN PATENT DOCUMENTS

| | | |
|---|---|---|
| JP | 10-175954 | 6/1996 |
| JP | 9-221473 | 8/1997 |
| JP | 10-158244 | 6/1998 |
| WO | WO 97/09981 | 3/1997 |
| WO | WO 99/25690 | 5/1999 |

OTHER PUBLICATIONS

Ikawa, M., Arch. Biochem. Biophys. 118(2) 497–500, 1967. CA PLUS Abstract provided.*
Buffoni et al. J. Enzyme Inhibition 8, 267–270, 1995.*
Cohen and Ziyadeh, 1996, *J. Amer. Soc. Nephrol.*, 7:183–190.
Colaco and Harrington, 1994, *NeuroReport*, 5: pp. 859–861.
Vlassara, Bucala & Striker, 1994, *Lab. Invest.*, 70: pp. 138–151.
Vlassara et al., 1994, *PNAS(USA)*, 91: pp. 11704–11708.
Daniels & Hauser, 1992, *Diabetes*, 41: pp. 1415–1421.
Brownlee, 1994, *Diabetes*, 43: pp. 836–841.
Cohen et al., 1994, *Kidney Int.*, 45: pp. 1673–1679.
Brett et al., 1993, *Am. J. Path.*, 143: pp. 1699–1712.
Yan et al., 1994, *PNAS(USA)*, 91: pp. 7787–7791.
Brownlee et al., 1983, *J. Exp. Med.*, 158: pp. 1739–1744.
Lamb et al., 1995, *Kidney Int.*, 47: pp. 1768–1774.
Motomiya et al., 1998, *Kidney Int'l.*, 54: pp. 1357–1366.
Friedlander et al., 1996, *J. Clin. Invest.*, 97: pp. 728–735.
Nakayama et al., 1997, *Kidney Int'l.*, 51: pp. 182–186.
Korbet et al., 1993, *Am. J. Kidney Disease*, 22: pp. 588–591.
Dawnay & Millar, (1998), Cell. Mol. Biol., 44: pp. 1081–1094.
Linden et al., (1998), Perit. Dial. Int., 18: pp. 290–293.
Hunt et al., (1988), Biochem., 256: pp. 205–212.
Berge et al., (1977), J. Pharm. Sci., 66: pp. 1–19.
Ikawa, (1967), Arch. Of Biochem. and Biophys., 118: pp. 497–500.
Borenfreund, (1984), J. Tissue Culture Methods, 9: pp. 7–9.
Heimann, et al., (1983), Cancer Res., 43: pp. 4856–4862.
Shopsis, et al., (1988), Alternative Methods in Toxicology, 6: 253–263.
Saxena, et al., (1980), Indian Journal of Chemistry, 19B: pp. 873–878.

* cited by examiner

*Primary Examiner*—Mukund J. Shah
*Assistant Examiner*—Venkataraman Balasubrasubramanian
(74) *Attorney, Agent, or Firm*—McDonnell Boehnen Hulbert & Berghoff; David S. Harper (57) ABSTRACT

The present invention provides novel compounds, pharmaceutical compositions, methods, and kits for inhibiting the conversion of Amadori compounds to post Amadori advanced glycation endproducts, and for treating and preventing chronic tissue damage and diabetic complication

11 Claims, 2 Drawing Sheets

POST-AMADORI INHIBITORS OF ADVANCED GLYCATION REACTIONS

CROSS REFERENCE

This application claims priority from U.S. Provisional Patent Application Serial No. 60/123,011 filed Mar. 5, 1999, and is related in subject matter to U.S. patent application Ser. No. 08/711,555 filed Sep. 10, 1996, now U.S. Pat. No. 5,985,857, and to pending U.S. application Ser. No. 08/971,285 (filed Nov. 17, 1997); U.S. patent application Ser. No. 09/322,569 (filed May 28, 1999); U.S. patent application Ser. No. 09/414,877 (filed Oct. 8, 1999); U.S. patent application Ser. No. 09/416,915 (filed Oct. 13, 1999); and U.S. patent application Ser. No. 09/422,615 (filed Oct. 21, 1999); the disclosures of which are incorporated by reference herein in their entirety.

FIELD OF THE INVENTION

The instant invention is in the field of inhibition of Advanced Glycation End-products formation, and the treatment and prevention of chronic tissue damage and diabetic complications.

BACKGROUND OF THE INVENTION

The elucidation of the pathogenic mechanisms of hyperglycemia is critical for developing rational therapy for the prevention of chronic tissue damage and diabetic complications, such as proteinuria, impaired glomerular clearance, nephropathy leading to end stage renal disease, protein cross-linking, retinopathy, and atherosclerotic disease. However, there is no consensus at present on the relative importance of the different possible pathogenic mechanisms that potentially contribute to these diabetic complications.

Nonenzymatic glycation by glucose and other reducing sugars is an important post-translational modification of proteins that has been increasingly implicated in diverse pathologies. Irreversible, nonenzymatic glycation and crosslinking through a slow, glucose-induced process may mediate many of the complications associated with diabetes. Chronic hyperglycemia associated with diabetes can cause chronic tissue damage which can lead to complications such as retinopathy, nephropathy, and atherosclerotic disease. (Cohen and Ziyadeh, 1996, *J. Amer. Soc. Nephrol.* 7:183–190). Clinically, diabetic nephropathy is defined by the presence of:

1. decrease in renal function (impaired glomerular clearance)
2. an increase in urinary protein (proteinuria)
3. the simultaneous presence of hypertension.

Nonenzymatic glycation of proteins, lipids, and nucleic acids may also play an important role in the natural processes of aging. Recently, protein glycation has been associated with β-amyloid deposits and formation of neurofibrillary tangles in Alzheimer disease, and possibly other neurodegenerative diseases involving amyloidosis (Colaco and Harrington, 1994, *NeuroReport* 5:859–861). Glycated proteins have also been shown to be toxic, antigenic, and capable of triggering cellular injury responses after uptake by specific cellular receptors (see for example, Vlassara, Bucala & Striker, 1994, *Lab. Invest.* 70:138–151; Vlassara et al., 1994, *PNAS(USA)*91:11704–11708; Daniels & Hauser, 1992, *Diabetes* 41:1415–1421; Brownlee, 1994, *Diabetes*43:836–841; Cohen et al., 1994, *Kidney Int.* 45:1673–1679; Brett et al., 1993, *Am. J. Path.* 143:1699–1712; and Yan et al., 1994, *PNAS(USA)* 91:7787–7791).

It has been shown that the resulting chronic tissue damage associated with long term diabetes mellitus arise in part from in situ immune complex formation by accumulated immunoglobulins and/or antigens bound to long-lived structural proteins that have undergone Advanced Glycosylation End-product (AGE) formation, via non-enzymatic glycosylation (Brownlee et al., 1983, *J. Exp. Med.* 158:1739–1744).

It has also been demonstrated that formation of AGE products occurs in dialysis fluid in vitro. (Lamb et al., Kidney Intl. 47:1768–1774 (1995). Furthermore, the level of various AGE species is increased in blood of patients on maintenance hemodialysis (Motomiya et al., Kidney Intl. 54:1357–1366 (1998)), and various studies indicate that glycosylation of peritoneal components occurs during peritoneal dialysis. (See. for example, Friedlander et al., J. Clin. Invest. 1996. 97:728–735; Nakayama et al., Kidney Intl. 51:182–186 (1997); and Korbet et al., Am. J. Kidney Disease 22:588–591 (1993) These studies have implicated accumulation of AGEs in the following pathologies in patients receiving dialysis:

1. Increased cardiac morbidity and mortality (Korbet et al., 1993)
2. Dialysis-related amyloidosis (Motomiya et al., Kidney Intl. 54:1357–1366, (1998)
3. Increased permeability of the peritoneal membrane (Nakayama et al., 1997)
4. Renal failure progression (Dawnay and Millar, Cell. Mol. Biol. 44:1081–1094 (1998) (increased rate to end-stage renal disease)
5. Ultrafiltration failure and peritoneal membrane destruction (Linden et al., Perit. Dial. Int. 18:290–293 (1998)

Figure 1:
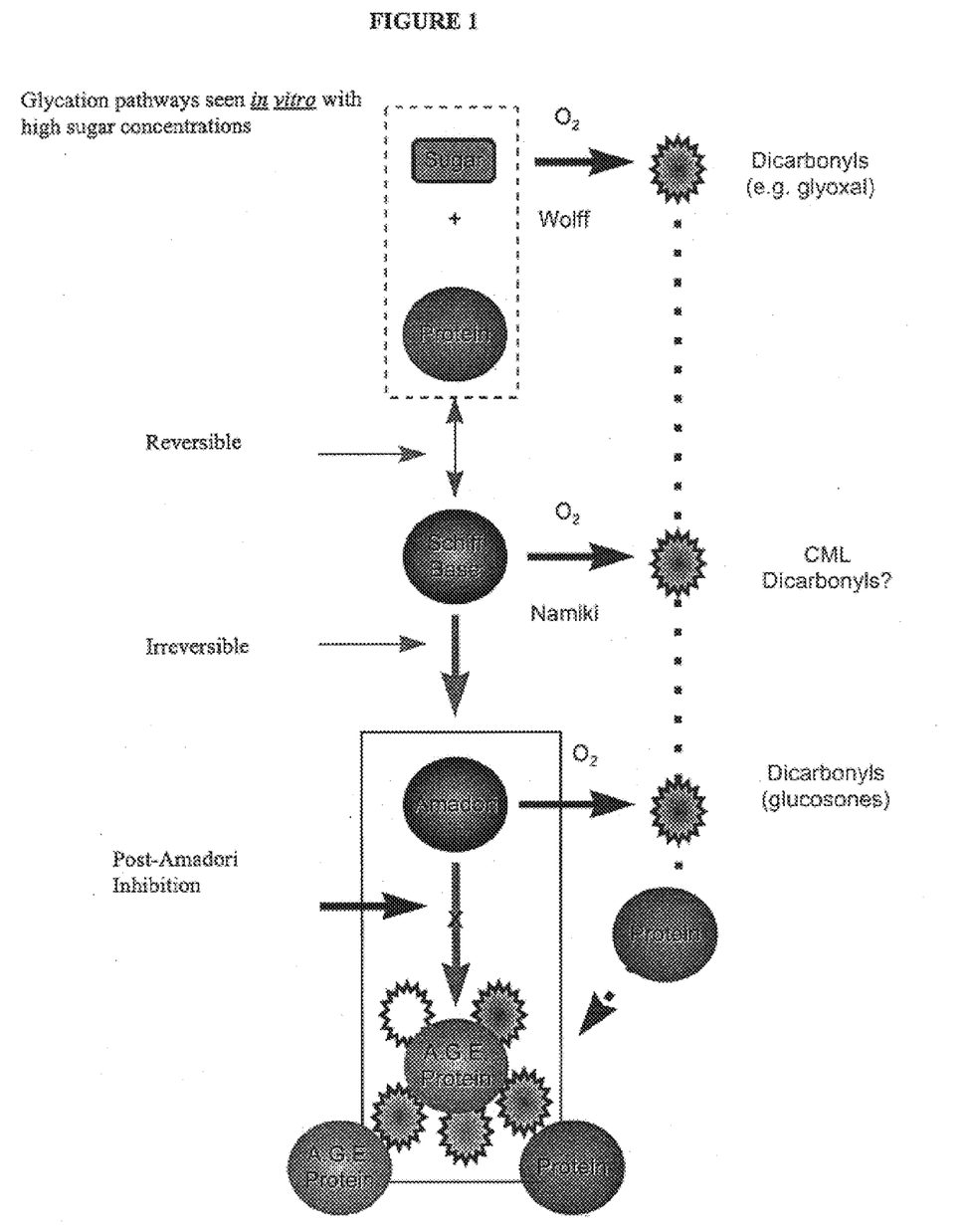
FIG. 1 is a flow chart of the glycation pathways seen in vitro with high sugar concentrations.

FIG. 1 is a flow chart of the glycation pathways seen in vitro with high sugar concentrations. Schiff bases and Amadori compounds are referred to as "early intermediates/products", while post-Amadori rearrangements leading to AGEs are referred to as "late intermediates/products" in these pathways. (See also U.S. Pat. No. 5,985,857.) The Amadori intermediates represent a crucial juncture where the "classical" pathway of nonenzymatic glycation begins to become essentially irreversible. In early inhibition studies, "glycation" was usually measured either as Schiff base formed (after reduction with labeled cyanoborohydride) or as Amadori product formed (after acid precipitation using labeled sugar). Such assays do not yield information on inhibition of post-Amadori conversion steps to "late" post-Amadori AGE products, since such steps lead to no change in the amount of labeled sugar that is attached to the proteins. Other "glycation" assays have relied on the sugar-induced increase of non-specific protein fluorescence, but this can also be induced by dicarbonyl oxidative fragments of free sugar, such as glycoaldehyde or glyoxal (Hunt et al., 1988, *Biochem.* 256:205–212), independently of Amadori product formation.

We have previously disclosed the use of pyridoxamine and derivative compounds to inhibit the conversion of Amadori compounds to post Amadori AGEs and to treat and prevent chronic tissue damage and diabetic complications such as proteinuria, impaired glomerular clearance, diabetic nephropathy, and protein cross-linking. (U.S. Pat. No. 5,985,857 and U.S. patent application Ser. No. 08/971,285 (filed Nov. 17, 1997) and U.S. patent application Ser. No. 09/322,569 (filed May 28, 1999), all references herein incorporated in their entirety.) We have also previously shown that pyridoxamine inhibits the formation of AGEs in peritoneal dialysis fluid (U.S. patent application Ser. No. 60/127,906, filed Apr. 6, 1999).

However, there remains a need in the art for novel compounds and methods for inhibiting AGE formation and for treating and preventing chronic tissue damage and diabetic complications.

SUMMARY OF THE INVENTION

The present invention provides novel compounds, pharmaceutical compositions, methods, kits, and dialysis solutions for inhibiting the conversion of Amadori compounds to post Amadori advanced glycation endproducts, for treating and preventing chronic tissue damage and diabetic complications, and for inhibiting dialysis-related pathologies, each method comprising administering to a mammal an amount effective to cause the desired effect of a compound of the following general formula:

wherein R1, R1', R5, and R5' are independently selected from the group consisting of $(CH_2)_nX$ wherein n is between 0 and 6 and X is H, OH, SH, COOH or $NH_2$; and mono-, di-, or tri-halogenated C1–6 alkyl, C1–6 alkoxy, or C1–6 alkenyl; with the proviso that at least one R1, R1', R5, and R5' is selected from the group consisting of OH, SH, and $NH_2$;

wherein R2, R2', R4 and R4' are independently selected from the group consisting of $(CH2)_nZ$, wherein n has the meaning given above and Z is H, OH, SH, COOH, or $NH_2$; and mono-, di-, or tri-halogenated C1–6 alkyl, C1–6 alkoxy, or C1–6 alkenyl;

wherein R3 and R3' are independently selected from the group consisting of H and mono-, di-, or tri-halogenated C1–6 alkyl;

wherein R6 and R6' are $(CH_2)x$, wherein x is between 1 and 6;

wherein R7 is selected from NH and HOP=O;

or wherein R6, R6' and R7 combine to form an aryl group, heteroaryl group, or or a pharmaceutically acceptable salt, ester, amide, or prodrug thereof.

DETAILED DESCRIPTION OF THE PREFERRED EMBODIMENTS

All references cited herein are incorporated by reference in their entirety.

The present invention fulfills a need in the art for novel compounds and methods for inhibiting the conversion of Amadori compounds to post Amadori advanced glycation endproducts, and for treating and preventing chronic tissue damage and diabetic complications including but not limited to proteinuria, impaired glomerular clearance, and diabetic nephropathy.

Thus, in one aspect the present invention provides novel compounds of the general formnula:

wherein R1, R1', R5, and R5' are independently selected from the group consisting of $(CH_2)_nX$ wherein n is between 0 and 6 and X is H, OH, SH, COOH or $NH_2$; and mono-, di-, or tri-halogenated C1–6 alkyl, C1–6 alkoxy, or C1–6 alkenyl; with the proviso that at least one R1, R1', R5, and R5' is selected from the group consisting of OH, SH, and $NH_2$;

wherein R2, R2', R4 and R4' are independently selected from the group consisting of $(CH2)_nZ$, wherein n has the meaning given above and Z is H, OH, SH, COOH, or $NH_2$; and mono-, di-, or tri-halogenated C1–6 alkyl, C1–6 alkoxy, or C1–6 alkenyl;

wherein R3 and R3' are independently selected from the group consisting of H and mono-, di-, or tri-halogenated C1–6 alkyl;

wherein R6 and R6' are $(CH_2)x$, wherein x is between 1 and 6;

wherein R7 is selected from NH and HOP=O;

or wherein R6, R6', and R7 combine to form an aryl group, heteroaryl group, or or a pharmaceutically acceptable salt, ester, amide, or prodrug thereof;

wherein the compound is not dipyridoxylamine.

In a preferred embodiment, R7 is NH; or R6, R6', and R7 combine to form an aryl group or a heteroaryl group. In a more preferred embodiment, R7 is NH.

In another preferred embodiment, both R1 and R1', or both R5 and R5' are selected from the group consisting of OH, SH, and $NH_2$.

In a further preferred embodiment, R6 and R6' are both $CH_2$.

In another preferred embodiment, R1 and R1' are identical; R2 and R2' are identical; R3 and R3' are identical; R4 and R4' are identical; R5 and R5' are identical; and R6 and R6' are identical.

Unless indicated otherwise, the alkyl, alkoxy, and alkenyl group substituents herein can be optionally substituted with at least one group independently selected from hydroxyl, carboxyl, amine, halogen, or aryl, or heteroaryl groups, which also may be optionally substituted.

By "alkyl" in the present invention is meant straight or branched chain alkyl groups having 1–10 carbon atoms, such as preferably $C_1$–$C_6$, methyl, ethyl, n-propyl, isopropyl, n-butyl, sec-butyl, tert-butyl, pentyl, 2-pentyl, isopentyl, neopentyl, hexyl, 2-hexyl, 3-hexyl, decyl, octyl, and 3-methylpentyl. These groups may be substituted, for instance with halo, alkyl, amino, alkylamino, dialkylamino, hydroxy, alkoxy and the like. Examples include chloromethyl, 2-amino ethyl, and 3-dimethyl-aminopropyl.

By "alkenyl" is meant straight or branched chain alkyl groups having 1–10 carbon atoms and having one or two nonadjacent double bonds. Examples of alkenyls include, but are not limited to, 3-butenyl and 1-methyl-3-pentenyl.

By "alkoxy" in the present invention is meant straight or branched chain alkoxy groups having 1–10 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By halogen in the present invention is meant fluorine, bromine, chlorine, and iodine.

The term "aryl" means an unsubstituted aromatic carbocyclic group having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl). The term "substituted aryl" means, unless stated otherwise, an aryl substituted by 1 to 4 substituents selected from alkyl, O-alkyl and S-alkyl, —OH, —SH, —CN, halogen, 1,3-dioxolanyl, —CF$_3$, —NO$_2$, —NH$_2$, —NHCH$_3$, —N(CH$_3$)$_2$, —NHCO-alkyl, —(CH$_2$)$_m$CO$_2$H, —(CH$_2$)$_m$CO$_2$-alkyl, —(CH$_2$)$_m$SO$_3$H, —NH alkyl, —NH alkyl, —N(alkyl)$_2$, —CH$_2$)$_m$PO$_3$H$_2$, —(CH$_2$)$_m$PO$_3$(alkyl)$_2$, —(CH$_2$)$_m$SO$_2$NH$_2$, and —(CH$_2$)$_m$SO$_2$NH-alkyl wherein alkyl is defined as above and m is 0, 1, 2, or 3.

By "heteroaryl" is meant one or more aromatic ring systems of 5-, 6-, or 7-members containing at least one and up to four heteroatoms selected from nitrogen, oxygen, or sulfur. Such heteroaryl groups include, for example, thienyl, furanyl, thiazolyl, imidazolyl, (is)oxazolyl, tetrazolyl, pyridyl, pyridonyl, pyrimidinyl, pyrazole, (iso)quinolinyl, napthyridinyl, phthalimidyl, benzimidazolyl, benzoxazolyl. A "substituted heteroaryl" group can be substituted with one, two, three, or four of the groups mentioned above for "substituted aryl", such as 2,3,4,6-tetrachloropyridyl and 2-methoxy-3-trifluoromethylthien-4-yl.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J Pharm. Sci.*, 1977;66:1–19 which is incorporated herein by reference.)

Examples of pharmaceutically acceptable, non-toxic esters of the compounds of this invention include $C_1$–$C_6$ alkyl esters, wherein the alkyl group is a straight or branched, substituted or unsubstituted, $C_5$–$C_7$ cycloalkyl esters, as well as arylalkyl esters such as benzyl and triphenylmethyl. $C_1$–$C_4$ alkyl esters are preferred, such as methyl, ethyl, 2,2,2-trichloroethyl, and tert-butyl. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines, wherein the alkyl groups are straight or branched. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

Especially preferred embodiments of this aspect of the invention are:

-continued

-continued

Further especially preferred embodiments can be derived by substituting either NH₂ or SH for the R5 and/or R5' substituents shown in the above specific embodiments.

In another aspect of the present invention, novel pharmaceutical compositions are provided, comprising an amount effective to inhibit AGE formation and/or to prevent or treat chronic tissue damage or diabetic complications of a compound of the general formula:

wherein R1, R1', R5, and R5' are independently selected from the group consisting of $(CH_2)_nX$ wherein n is between 0 and 6 and X is H, OH, SH, COOH or NH$_2$; and mono-, di-, or tri-halogenated C1–6 alkyl, C1–6 alkoxy, or C 1–6 alkenyl; with the proviso that at least one R1, R1', R5, and R5' is selected from the group consisting of OH, SH, and NH$_2$;

wherein R2, R2', R4 and R4' are independently selected from the group consisting of (CH2)$_n$Z, wherein n has the meaning given above and Z is H, OH, SH, COOH, or NH$_2$; and mono-, di-, or tri-halogenated C1–6 alkyl, C1–6 alkoxy, or C1–6 alkenyl;

wherein R3 and R3' are independently selected from the group consisting of H and mono-, di-, or tri-halogenated C1–6 alkyl;

wherein R6 and R6' are (CH$_2$)x, wherein x is between 1 and 6;

wherein R7 is selected from NH and HOP=O;

or wherein R6, R6', and R7 combine to form an aryl group, heteroaryl group, or or a pharmaceutically acceptable salt, ester, amide, or prodrug thereof, and a pharmaceutically acceptable carrier.

In various preferred embodiments of the pharmaceutical composition, R7 is NH, or R6, R6', and R7 combine to form an aryl group or a heteroaryl group; R1 and R1', or R5 and R5' are both selected from the group consisting of OH, SH, and NH$_2$; and/or R6 and R6' are both CH$_2$.

In another preferred embodiment, R1 and R1' are identical; R2 and R2' are identical; R3 and R3' are identical; R4 and R4' are identical; R5 and R5' are identical; and R6 and R6' are identical.

Especially preferred embodiments of the pharmaceutical compositions comprise the following compounds:

Dipyridoxylamine (BST 4500)

-continued

Dipyridoxylamine (also referred to herein as BST 4500) and its synthesis have been disclosed (Ikawa, Arch. of Biochem. and Biophys., 118:497–500 (1967)), but the present invention demonstrates its first therapeutic use.

While not being limited by any particular mechanism, the above compounds possess similar activity to dipyridoxylamine, but may provide for increased solubility, transport, and absorption in a patient treated therewith.

In a further aspect, the present invention provides methods for inhibiting AGE formation and/or for preventing or treating chronic tissue damage or diabetic complications comprising administering to a mammal an amount effective to inhibit AGE formation and/or prevent or treat chronic tissue damage or diabetic complications of the compounds and pharmaceutical compositions of the invention.

In further aspects, the present invention provides methods for inhibiting dialysis-related pathologies, including but not limited to cardiac morbidity and mortality, dialysis-related amyloidosis, dialysis-related increases in permeability of the peritoneal membrane in a patient, renal failure progression, ultrafiltration failure, and peritoneal membrane destruction in a patient, comprising introducing into the patient a dialysis solution that comprises an amount of the compounds or pharmaceutical compositions of the present invention sufficient to inhibit or limit the specified endpoint. The invention further provides improved dialysis solutions, wherein the improvement comprises the addition of an amount effective to inhibit post-Amadori AGE formation of the compounds or phannaceutical compositions of the invention to dialysis fluid.

The invention further provides kits for inhibiting AGE formation and/or for preventing or treating chronic tissue damage or diabetic complications comprising packaging material, the above pharmaceutical composition, and/or instructions for using the pharmaceutical compositions to carry out the methods of the invention.

The instant compounds can be administered individually or in combination, usually in the form of a pharmaceutical composition. Such compositions are prepared in a manner well known in the pharmaceutical art and comprise at least one active compound.

The compounds of the invention can be administered as the sole active pharmaceutical agent, or they can be used in combination with one or more other anti-AGE agents, including but not limited to pyridoxamine and aminoguanidine. When administered as a combination, the therapeutic agents can be formulated as separate compositions that are given at the same time or different times, or the therapeutic agents can be given as a single composition.

The compounds may be made up in a solid form (including granules, powders or suppositories) or in a liquid form (e.g., solutions, suspensions, or emulsions). The compounds of the invention may be applied in a variety of solutions and may be subjected to conventional pharmaceutical operations such as sterilization and/or may contain conventional adjuvants, such as preservatives, stabilizers, wetting agents, emulsifiers, buffers etc.

For administration, the compounds are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Pharmaceutical compositions containing the compounds described herein are administered to an individual in need thereof. In therapeutic applications, compositions are administered to a mammalian patient in an amount sufficient to inhibit post-Amadori AGE fonnation or to treat and/or prevent diabetic complications. Amounts effective for this use depend on factors including, but not limited to, the nature of the compound (specific activity, etc.), the route of administration, the stage and severity of the disorder, the weight and general state of health of the mammal, and the judgment of the prescribing physician. The active compounds are effective over a wide dosage range. However, it will be understood that the amount of the compound actually administered will be determined by a physician, in the light of the above relevant circumstances. Therefore, the above dosage ranges are not intended to limit the scope of the invention in any way.

The compounds of the invention may be administered by any suitable route, including orally, parentally, by inhalation or rectally in dosage unit formulations containing conventional pharmaceutically acceptable carriers, adjuvants, and vehicles, including liposomes. The term parenteral as used herein includes, subcutaneous, intravenous, intraarterial, intramuscular, intrasternal, intratendinous, intraspinal, intracranial, intrathoracic, infusion techniques, intracavity, or intraperitoneally. In a preferred embodiment, the compounds of the invention are administered orally or parentally.

The instant invention may be embodied in other forms or carried out in other ways without departing from the spirit or essential characteristics thereof. The present disclosure and enumerated examples are therefore to be considered as in all respects illustrative and not restrictive, the scope of the invention being indicated by the appended claims, and all equivalencies are intended to be embraced therein. One of ordinary skill in the art would be able to recognize equivalent embodiments of the instant invention, and be able to practice such embodiments using the teaching of the instant disclosure and only routine experimentation.

EXAMPLES

Figure 2:
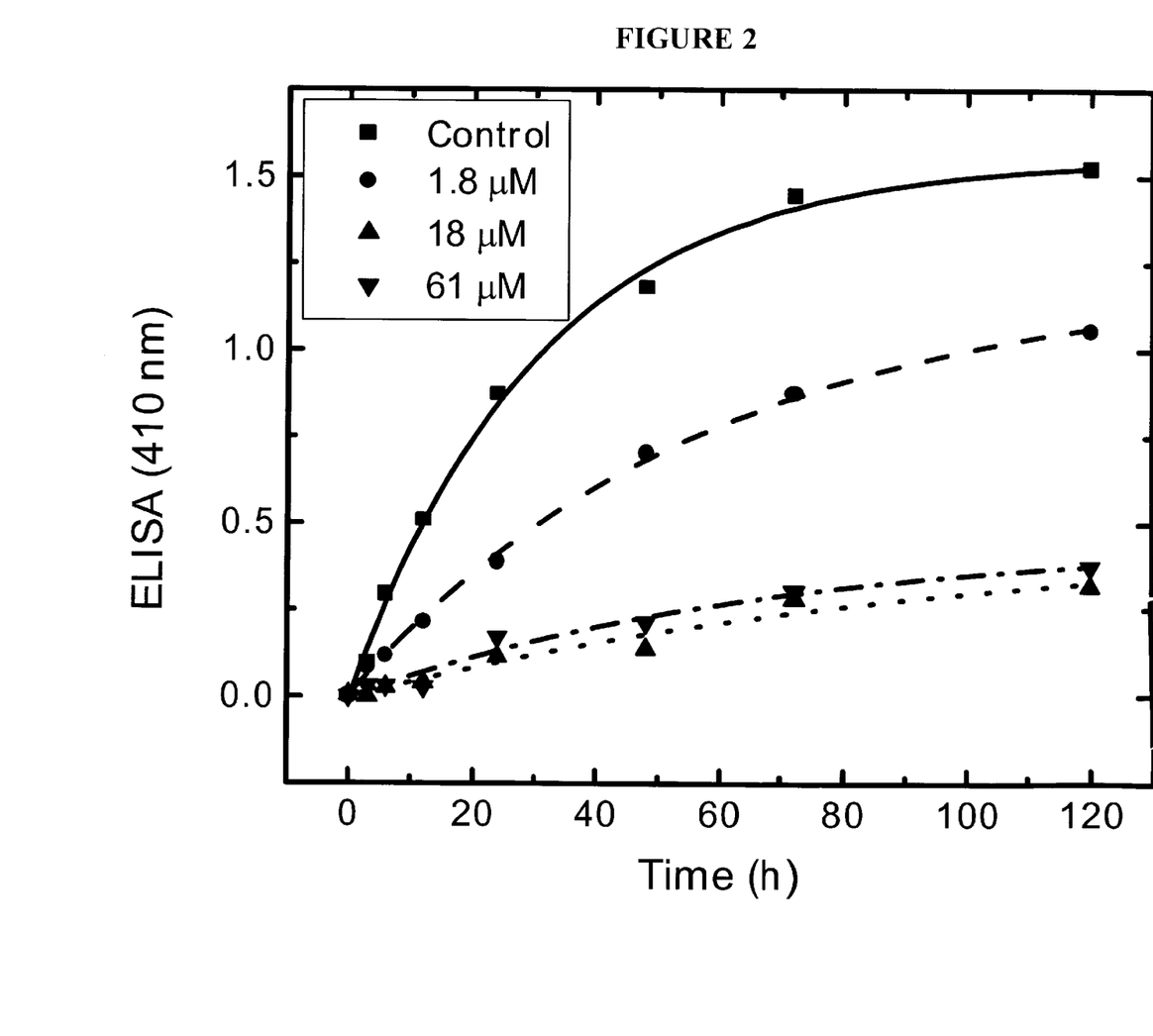
FIG. 2 is graph depicting the effect of BST-4500 on advanced glycation endproduct formation during interrupted glycation (Post-amadori reaction) of bovine serum albumin by ribose.

FIG. 2 is graph depicting the effect of dipyridoxylamine (BST-4500) on post-Amadori AGE formation during interrupted glycation of bovine serum albumin by ribose. Modification with ribose was done at 37° C. in 0.2 M phosphate buffer of pH 7.5 containing 0.02% sodium azide. The solutions were kept in capped tubes and opened only to remove timed aliquots that were immediately frozen for later carrying out the various analyses. "Interrupted glycation" experiments were carried out by first incubating protein with the ribose at 37° C. for 8 or 24 h, followed by immediate and extensive dialysis against frequent cold buffer changes at 4° C. The samples were then reincubated by quickly warming to 37° C. in the absence of external ribose. Aliquots were taken and frozen at various intervals for later analysis.

The interrupted glycation method for following post-Amadori kinetics of AGE formation allows for the rapid quantitative study of "late" stages of the glycation reaction. Importantly, this method allows for inhibition studies that are free of pathways of AGE formation which arise from glycoxidative products of free sugar or Schiff base (Namiki pathway).

These data demonstrate that dipyridoxylamine is very effective at inhibiting the conversion of Amadori compounds to post Amadori advanced glycation endproducts with a half-maximal inhibitory concentration of approximately 4 $\mu$M. In comparison, in a similar experiment, pyridoxamine inhibited the conversion of Amadori compounds to post Amadori advanced glycation endproducts with a half-maximal inhibitory concentration of approximately 3 mM. Thus, the post-Amadori-inhibitory activity of dipyridoxylaminc is approximately 750-fold greater than that of pyridoxamine.

A neutral red uptake bioassay using normal human epidermal keratinocytes was then conducted to preliminarily estimate the toxicity (HuLC50) of dipyridoxylamine relative to pyridoxamine. The bioassay was conducted according to standard protocols. (Borenfreund et al., J. Tissue Culture Methods 9:7–9, 1984; Heimann, et al., Cancer Res. 43:4856–4862, 1983; Shopsis et al., in "Alternative Methods in Toxicology," Vol. 6, AM Goldberg (Ed), Mary Ann Liebert, Inc., N.Y., p. 253–263, 1988) The preliminarily estimated concentration for half-maximal toxicity was then divided by the half maximal inhibition of post-Amadori AGE formation to derive a therapeutic index ratio. The results are shown in Table 1:

TABLE 1

| Inhibitor | Therapeutic Index Ratio | | |
|---|---|---|---|
| | HuLC50 | IC50 | Therapeutic Index |
| Dipyridoxylamine | 0.0018M | 0.000004M | 450 |
| Pyridoxamine | 0.0167M | 0.003M | 5.57 |

These data demonstrate that, although dipyridoxylamine appears to be mildly more toxic than pyridoxamine in the above assay, its activity in inhibiting post-Amadori AGE formation is so much greater than pyridoxamine that it possesses a substantially superior therapeutic index ratio, and thus may be a superior therapeutic option than pyridoxamine.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention

We claim:

1. A pharmaceutical composition comprising an amount effective to inhibit the conversion of Amadori compounds to post-Amadori advanced glycation endproducts or for treating or preventing an AGE-related pathology selected from the group consisting of proteinuria, impaired glomerular clearance, diabetic nephropathy, and protein cross-linking, of a compound of the formula wherein R1, R1', R5, and R5' are independently selected from the group consisting of $(CH_2)_nX$ wherein n is between 0 and 6 and X is selected from the group consisting of H, OH, $CH_2OH$, and mono-, di-, or tri-halogenated C1–6 alkyl; with the proviso that at least one of R1, R1', R5, and R5' is OH;

wherein R2, R2', R4 and R4' are independently selected from the group consisting of $(CH2)_nZ$, wherein n has the meaning given above and Z is selected from the group consisting of H, OH, and mono-, di-, or tri-halogenated C1–6;

wherein R3 and R3' are independently selected from the group consisting of H and mono-, di-, or tri-halogenated C1–6 alkyl;

wherein R6 and R6' are $(CH_2)x$, wherein x is between 1 and 6;

wherein R7 is selected from NH and HOP=O;

or wherein R6, R6', and R7 combine to form an aryl group, heteroaryl group, or or a pharmaceutically acceptable salt or prodrug thereof; and a pharmaceutically acceptable carrier.

2. The pharmaceutical composition of claim 1 wherein the compound is of the formula wherein R1, R1', R5, and R5' are independently selected from the group consisting of $(CH_2)_nX$ wherein n is between 0 and 6 and X is selected from the group consisting of H, OH, $CH_3$, or $CH_2OH$ with the proviso that at least one of R1, $R_1$', R5, and R5' is OH;

wherein R2, R2', R4 and R4' are independently selected from the group consisting of $(CH2)_nZ$, wherein n has the meaning given above and Z is selected from the group consisting of H, OH, or $CH_3$;

wherein R3 and R3' are independently selected from the group consisting of H or $CH_3$;

wherein R6 and R6' are $(CH_2)x$, wherein x is between 1 and 6;

wherein R7 is selected from NH and HOP=O;

or wherein R6, R6', and R7 combine to form an aryl group, heteroaryl group, or or a pharmaceutically acceptable salt, or prodrug thereof; and a pharmaceutically acceptable carrier.

3. The pharmaceutical composition of claim 1 wherein the compound is selected from the group consisting of:

-continued

-continued

4. A method for inhibiting the conversion of Amadori compounds to post Amadori advanced glycation endproducts in a mammal comprising administering to a mammal an amount effective to inhibit the conversion of Amadori compounds to post Amadori advanced glycation endproducts, of a pharmaceutical composition of any one of claims 1–3.

5. A method for treating or preventing an AGE related pathology in a mammal comprising administering to a mammal an amount effective to treat or prevent the AGE-related pathology of a pharmaceutical composition of any one of claims 1–3, wherein the AGE-related pathology is selected from the group consisting of proteinuria, impaired glomerular clearance, diabetic nephropathy, and protein cross-linking.

6. The method of claim 5 wherein the mammal has an elevated blood sugar level.

7. An improved dialysis solution, wherein the improvement comprises the addition of an amount effective to inhibit post-Amadori AGE formation, of a pharmaceutical composition of any one of claims 1–3.

8. The pharmaceutical composition of claim 1, wherein the compound comprises dipyridoxylamine.

9. The method of claim 4 wherein the pharnaceutical composition comprises dipyridoxylamine.

10. The method of claim 5 wherein the pharmaceutical composition comprises dipyridoxylamine.

11. An improved dialysis solution, wherein the improvement comprises the addition of an amount of dipyridoxylamine effective to inhibit post-Amadori AGE formation.

* * * * *